US006187934B1

(12) United States Patent
Tsuji et al.

(10) Patent No.: US 6,187,934 B1
(45) Date of Patent: Feb. 13, 2001

(54) TITANIUM-CONTAINING SOLID CATALYST

(75) Inventors: Junpei Tsuji, Chiba; Kenshi Uchida, Kanagawa; Masaru Ishino, Chiba, all of (JP)

(73) Assignee: Sumitomo Chemical Company Limited, Osaka (JP)

( * ) Notice: Under 35 U.S.C. 154(b), the term of this patent shall be extended for 0 days.

(21) Appl. No.: 09/045,874

(22) Filed: Mar. 23, 1998

(30) Foreign Application Priority Data

| Mar. 26, 1997 | (JP) | 9-073719 |
| Mar. 28, 1997 | (JP) | 9-077059 |
| Apr. 9, 1997 | (JP) | 9-090779 |

(51) Int. Cl.$^7$ ................................................ C07D 301/19
(52) U.S. Cl. ................................................................ 549/529
(58) Field of Search ............................................. 549/529

(56) References Cited

U.S. PATENT DOCUMENTS 3,923,843   12/1975   Wulff ................................. 260/348.5

FOREIGN PATENT DOCUMENTS

| 0 323 663 A2 | 7/1989 | (EP) . |
| 0 345 856 | 12/1989 | (EP) . |
| 0 368 656 A2 | 5/1990 | (EP) . |
| 0 734 764 | 10/1996 | (EP) . |
| 50-30049 | 9/1975 | (JP) . |
| 54-40525 | 12/1979 | (JP) . |
| 54-40526 | 12/1979 | (JP) . |
| 56-35941 | 8/1981 | (JP) . |

*Primary Examiner*—Ba K. Trinh
(74) *Attorney, Agent, or Firm*—Sughrue, Mion, Zinn, Macpeak & Seas, PLLC

(57) ABSTRACT

A titanium-containing solid catalyst used for producing an oxirane compound by reacting an olefin type compound with an organic hydroperoxide, wherein the catalyst is obtainable by at least one method selected from the following (1) to (3):

(1) a titanium compound is supported on silica having an average pore diameter (D) measured by a mercury pressing method of 5 nm or more and having pore distribution in which at least 60% of pore volume is composed of pores having a pore diameter within the range of D±0.3 D (nm), and is calcined (2) silica is impregnated in water, then dried, and a titanium compound is supported on the silica, then calcined, (3) silica is impregnated in a titanium-containing impregnation solution satisfying the following [formula-1], and is calcined $A/B \leq 0.2$ [formula-1]

A: mol number of metal titanium in the impregnation solution

B: mol number of a silanol group existing in silica.

10 Claims, No Drawings

TITANIUM-CONTAINING SOLID CATALYST

BACKGROUND OF THE INVENTION

1. Title of the Invention

The present invention relates a titanium-containing solid catalyst and a method for producing an oxirane compound. More particularly, the present invention relates to a titanium-containing solid catalyst used for producing an oxirane compound by reacting an olefin type compound with an organic hydroperoxide, the catalyst having high activity and enabling the intended conversion in a smaller reactor than that of a conventional method, and a method for producing an oxirane compound using said catalyst.

2. Description of the Related Art

A method for producing an oxirane compound by reacting anolefintypecompound withanorganic hydroperoxideusing a titanium-containing solid catalyst is well known (Japanese Patent Application Publication (JP-B) Nos. 56-35,941, 54-40,525, 54-40,526, 50-30,049, and Japanese Patent Application Laid-Open (JP-A) No. Hei 8-269,031).

A titanium-containing solid catalyst can be produced in various methods. For example, a production method in which a titanium compound is supported on silica and is calcined is one useful method. However, catalysts produced by the conventional methods have problems that activity is insufficient, an excessively large reaction vessel is required for industrial scale production, production cost is increased, and the like.

SUMMARY OF THE INVENTION

The present inventors have intensively studied a catalyst having no above-described problems, and found that a titanium-containing solid catalyst using specific silica or silica which has been specifically treated as a carrier, or a titanium-containing solid catalyst in which titanium content in a silica carrier is controlled in a specific range, is highly active when used in a method for producing an oxirane compound, and completed the present invention.

Namely, the present invention is a titanium-containing solid catalyst used for producing an oxirane compound by reacting an olefin type compound with an organic hydroperoxide, wherein the catalyst is obtainable by at least one method selected from the following (1) to (3):

(1) a titanium compound is supported on silica having an average pore diameter (D) measured by a mercury pressing method of 5 nm or more and having pore distribution in which at least 60% of pore volume is composed of pores having a pore diameter within the range of D±0.3 D (nm), and is calcined, (2) silica is impregnated in water, then dried, and a titanium compound is supported on the silica, then calcined, (3) silica is impregnated in a titanium-containing impregnation solution satisfying the following [formula-1], and is calcined $A/B \leq 0.2$ [formula-1]

A: mol number of metal titanium in the impregnation solution

B: mol number of a silanol group existing in silica.

As a titanium-containing solid catalyst of the present invention, there can be used a catalyst obtainable by a method in which (1) a titanium compound is supported on silica having an average pore diameter (D) measured by a mercury pressing method of 5 nm or more and having pore distribution in which at least 60% of pore volume is composed of pores having a pore diameter within the range of D±0.3 D (nm), and is calcined, The silica used contains silicon in the form of a dioxide preferably in an amount of 50% or more, more preferably 75% or more, and further preferably 90% or more. It is preferable that the silica used has relatively large specific surface area, and the specific surface area is preferably 1 $m^2/g$ or more, and more preferably 25 to 800 $m^2/g$.

The silica used is preferably porous synthetic silica of close packing type having relatively high density composed of an amorphous silica particle coagulated or bonding each other, and for example, silica gel and precipitated silica are listed. Production methods and properties thereof are described in R. G. Irer ed. "The ColloidChemistryof Silicaand Silicate" (Cornel University Publication Department, New York, USA, (1955)) chapter VI and U.S. Pat. No. 2,657,149. Among commercially available silica gels, silica gel having a specific surface area of 25 to 700 $m^2/g$, a pore volume of 0.3 to 2.0 ml/g, and a silica content of 99% by weight or more is preferable used.

Regarding the silica used, the average pore diameter (D) measured by a mercury pressing method is required to be 5 nm or more, preferably from 8 nm or more to 45 nm or less, and more preferably from 12 nm or more to 40 nm or less. When the average pore diameter (D) is less than 5 nm, activity remarkably decreases.

On the other hand, when the average pore diameter (D) is over 12 nm, selection ratio of an oxirane compound remarkably increases.

Further, the silica used is required to have pore distribution in which, based the average pore diameter (D) measured by a mercury pressing method, at least 60% of pore volume is composed of pores having a pore diameter within the range of D±0.3 D (nm), and it is preferable that the pore distribution of the silica is substantially uniform.

For supporting Ti, both a gas phase supporting method and a liquid phase supporting method can be applied. In the gas phase supporting, titanium salts and titanates of organic acids and inorganic acids, which are able to vaporize at supporting temperature, are applied. In the liquid phase supporting, titanium salts and titanates of organic acids and inorganic acids, which can be solved in a solvent, can be used.

Examples of the titanium compound include tetramethyl titanate, tetraethyl titanate, tetrapropyl titanate, tetraisopropyl titanate, tetrabutyl titanate, tetraisobutyl titanate, tetra-2-ethylhexyl titanate, tetraoctadecyl titanate, titanium tetrachloride, titanium tetrabromide, titaniumtetraiodide, titanium (IV) oxyacetyl acetonate, titanium (IV) diisopropoxidebisacetyl acetonate and the like. A multi-stage supporting method which includes or does not include a drying and/or calcining step can be used.

As a suitable supporting, washing solvent in the liquid-phase supporting, oxa and/or oxo substituted hydrocarbons which are liquid at ordinary temperature having 1 to about 12 carbon atoms can generally be used. As a suitable solvent, alcohols, ketones, ethers (non-cyclic or cyclic type) and esters can be used. Examples thereof include hydroxy-substituted hydrocarbons such as methanol, ethanol, ethylene glycol, propylene glycol, isopropanol, n-butanol and octanol; oxo-substituted hydrocarbons such as acetone, diethyl ketone, methyl ethyl ketone and methyl isobutyl ketone; hydrocarbon ethers such as diisobutyl ether and tetrahydrofuran; and hydrocarbon esters such as methyl acetate, ethyl acetate, butyl acetate and butyl propionate, and the like.

Following the liquid-phase supporting, it is preferable to remove the absorbed solvent. This solvent removing operation may include decantation, filtration, centrifugal separation, vacuum gas discharge, drying and other operations. In this solvent removing operation, conditions are selected so that an excess solvent for supporting is removed from silica in an amount preferably at least 80% and more preferable at least 95%.

As described in Japanese Patent Application Laid-Open (JP-A) No. Hei 8-269,031, it is preferable to conduct washing after liquid-phase supporting treatment. A solvent for washing and a catalyst after Ti supporting are fully mixed, then a liquid-phase portion is separated by a method such as filtration, decantation or the like. This sequence is repeated for required times. Completion of the washing can be known by analysis of the liquid-phase portion. The washing temperature is from preferably 0 to 100° C., more preferably from 10to 60° C. Aftercompletionof thewashing, the remaining solvent for washing is removed by the same method as that in the impregnating solvent removing process. This solvent removal is useful for recovering a large amount of the solvent, simultaneously for decreasing ignition danger in calcining period, and for preventing decrease in physical strength of a catalyst derived from rapid evaporation of a large amount of a volatile solvent in a catalyst composition during calcining at higher temperature thereafter. Drying at 25 to 200° C. is also effective as a solvent removing method.

After the Ti supporting, this catalyst composition is calcined. Namely, it is calcined under atmosphere of a non-reducing vapor, for example, nitrogen, argon or carbon dioxide, or an oxygen-containing vapor, for example, air. On the role of the calcining is to convert titanium in supported form, namely titanium halide, titanium alkanolate or the like to an insoluble chemically-bonded oxide. The other role of the calcining is to activate the catalyst. The calcining temperature may sufficiently be 400to 900° C., and a temperature from 400 to 800° C. is recommended. Usual calcining time is 1 to 18 hours.

As a titanium-containing solid catalyst of the present invention, there can also be used a catalyst which is obtainable by a method in which (2) silica is impregnated in water, then dried, and a titanium compound is supported on the silica, then calcined.

As the silica used, in addition to those used for the above-described method (1), the following compounds can be used.

A synthetic silica powder composed of an amorphous silica power which is produced by coagulation operation, has open-pack structure, is easily collapsed, and weakly bonded each other is also suitable as a carrier. For example, a fumed pyrogenic silica obtained by calcining operation of hydrogen and oxygen with silicon tetrachloride or silicon tetrafluoride is listed, and specifically, Cab-O-sil manufactured by Cabot Corp., Aerosil manufactured by Degussa Corp. and the like are listed ("Cab-O-sil" and "Aerosil" are registered trade mark). Among these silica products, a product having a specific surface area of 50 to 500 m$^2$/g and a silica content of 99% or more are preferably used.

Further, a crystalline porous silica can also preferably be used. As the crystalline porous silica, for example, high silica zeolite (other metal such as aluminum and the like is contained only in small amount) is listed. As example of the high silica zeolite, silicalite which is pentasil type zeolite, and the like are known (R. W. Grose and E. M. Flanigen, U.S. Pat. No. 4,061,724 (1977) (to UCC)). MCM 41 having regular micro-porous structure (J. S. Beck, et al., J. Am. Chem. Soc., 114, 10834 (1992)) can also be used as a carrier, though it is not crystalline material.

Before Ti is supported on these silicas, impregnation into water, and further, drying treatment are conducted.

Water used for impregnation of the silica is not particularly restricted. Neutral, acidic or alkaline water can be used.

When water is converted to acidic, an acid used is not particularly restricted, and for example, inorganic acids such as hydrochloric acid, sulfuric acid, nitric acid and the like, and organic acids such as formic acid, acetic acid, propionic acid, benzoic acid and the like, can be used.

Further, when water is converted to alkaline, a base used is not particularly restricted, and for example, inorganic bases such as ammonia, sodium hydroxide, potassium hydroxide and the like, and organic bases such as triethylamine and the like, can be used.

For the impregnation treatment, silica is impregnated in water, and is preferably left for 1 to 50 hours at 10 to 100° C. The impregnation treatment may be conducted in stationary condition, or may be conducted with stirring. After completion of the impregnation treatment, usually, water is removed by filtration and the like, solid is washed with water until the filtrate becomes neutral. Then, silica is dried preferably at 100 to 200° C. in vacuo or under air or nitrogen flow.

The Ti supporting method and the calcining method after the Ti supporting are the same as described above.

As a titanium-containing solid catalyst of the present invention, there can also be used a catalyst which is obtainable by a method in which (3) silica carrier is impregnated in a titanium-containing impregnation solution satisfying the following [formula-1] in liquid-phase supporting, dried, and the titanium compound is supported on the dried silica, then calcined $$A/B \leq 0.2 \text{ [formula-1]}$$

A: mol number of metal titanium in the impregnation solution

B: mol number of a silanol group existing in silica

The silica used is the same as that used in the above-described (2).

For Ti supporting, a liquid-phase supporting method is preferable. The kind of the Ti compound and the kind of the solvent used for the liquid-phase supporting are the same as described in the above-described (1).

In the liquid-phase supporting, silica carrier is impregnated in an titanium-containing impregnation solution satisfying the following [formula-1]:

$$A/B \leq 0.2 \text{ [formula-1]}$$

A: mol number of metal titanium in the impregnation solution

B: mol number of a silanol group existing in silica

When A/B is over 0.2, selectivity of an oxirane compound decreases. A/B is further preferably 0.15 or less, and most preferably 0.05 or less. Further, since titanium supporting amount is too small, activity decreases. So the minimum limit of A/B is preferably 0.005 or more.

The mol number of a silanol group on the carrier can be calculated by regarding reduction in weight of the silica at high temperature calcination (up to 1000° C.) as a condensation dehydration amount of the silanol group (JIS K 1150 Silica gel test method (1994)). It is also permissible that reduction in weight is measured by TG (thermogravimetric analysis), and the mol number is calculated in the same manner as in the above-described case.

Usually, 50 to 100% of metal titanium is supported on the resulting titanium-containing solid catalyst, though the amount differs depending on the impregnation condition or the following treating method.

There are two methods for controlling ratio of the mol number of metal titanium in the impregnation solution to the mol number of a silanol group on the carrier to preferable value. A first method is one in which the amount of metal titanium to be impregnated is defined, and a carrier having a silanol group in a number which is preferable for the amount of metal is selected. A second method is one in which the number of a silanol group on the carrier is measured, and the impregnation amount of metal titanium is controlled in preferable range.

The removal of a solvent, the washing of a catalyst after Ti supporting, and the calcination of a catalyst composition, following the liquid-phase supporting, are the same as described in the above-described case (1).

It is preferable that all catalysts obtained as described above are reacted with a silylating agent before use. Examples of the silylating agent include an organic silane, organic silylamine, organic silylamide and derivatives thereof, and organic silazane, and other silylating agents.

Examples of the organic silane include chlorotrimethylsilane, dichlorodimethylsilane, chlorobromodimethylsilane, nitrotrimethylsilane, chlorotriethylsilane, iododimethylbutylsilane, chlorodimethylphenylsilane, chlorodimethylsilane, dimethyl n-propylchlorosilane, dimethylisopropylchlorosilane, t-butyldimethylchlorosilane, tripropylchlorosilane, dimethyloctylchlorosilane, tributylchlorosilane, trihexylchlorosilane, dimethylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, methylphenylchlorosilane, triethoxychlorosilane, dimethylphenylchlorosilane, methylphenylvinylchlorosilane, benzyldimethylchlorosilane, diphenylchlorosilane, diphenylmethylchlorosilane, diphenylvinylchlorosilane, tribenzylchlorosilane, 3-cyanopropyldimethylchlorosilane and the like.

Examples of the organic silylamine include N-trimethylsilylimidazole, N-t-butyldimethylsilylimidazole, N-dimethylethylsilylimidazole, N-dimethyl n-propylsilylimidazole, N-dimethylisopropylsilylimidazole, N-trimethylsilyldimethylamine, N-trimethylsilyldiethylamine, N-trimethylsilylpyrrole, N-trimethylsilylpyrrolidine, N-trimethylsilylpiperidine, pentafluorophenyldimethylsilylamine, 1-cyanoethyl(diethylamino)dimethylsilane and the like.

Examples of the organic silylamide and derivatives thereof include N,O-bistrimethylsilylacetamide, N,O-bistrimethylsilyltrifluoroacetamide, N-trimethylsilylacetamide, N-methyl-N-trimethylsilylacetamide, N-methyl-N-trimethylsilyltrifluoroacetamide, N-methyl-N-trimethylsilylheptafluorobutylamide, N-(t-butyldimethylsilyl)-N-trifluoroacetamide, N,O-bis(diethylhydrosilyl)trifluoroacetamide and the like.

Examples of the organic silazane include hexamethyldisilazane, heptamethyldisilazane, 1,1,3,3-tetramethyldisilazane, 1,3-bis(chloromethyl) tetramethyldisilazane, 1,3-divinyl-1,1,3,3-tetramethyldisilazane, 1,3-diphenyltetramethyldisilazane and the like.

Examples of the other silylating agents include N-methoxy-N,O-bistrimethylsilyltrifluoroacetamide, N-methoxy-N,O-bistrimethylsilylcarbamate, N,O-bistrimethylsilylsulfamate, trimethylsilyltrifluoromethanesulfonate, N,N'-bistrimethylsilylurea and the like.

Among them, hexamethyldisilazane is preferably used.

Thus obtained catalyst can be used in any physical form such as, for example, a powder, flake, spherical particle and pellet.

The epoxidation reaction is conducted by reaction between an organic hydroperoxide with an olefin in the presence of a catalyst prepared in the above-described method.

The organic hydroperoxide is a compound having the general formula R—O—O—H (wherein, R represents a monovalent hydrocarbyl group.), and this is reacted with an olefin type compound to obtain an oxirane compound and a compound R—OH. R preferably represents a group having 3 to 20 carbon atoms, more preferably a hydrocarbyl group having 3 to 10 carbon atoms, and further preferably a secondary and tertiary alkyl group or aralkyl group. Among these groups, particularly preferable are a tertiary alkyl group, and a secondary or tertiary aralkyl group, and specific examples thereof include a tertiary butyl group, tertiary pentyl group, cyclopentyl group, 1-phenylethyl-1 group and 2-phenylpropyl-2 group, and further, various tetralinyl groups produced by removing a hydrogen atom from an aliphatic side chain of a tetralin molecule.

When an ethylbenzene hydroperoxide is used, the resulted hydroxyl compound is 1-phenylethanol, and this can be converted to styrene via dehydration reaction. When cumene hydroperoxide is used, the resulted hydroxyl compound is 2-phenyl-2-propanol. This can be converted to α-methylstyrene via dehydration reaction. Styrene and α-methylstyrene are both an industrially useful substance.

Tertiary amylene generated by dehydration reaction of tertiary pentyl alcohol obtained by using tertiary pentyl hydroperoxide is a substance which is useful as a precursor of isoprene. Tertiary pentyl alcohol is useful also as a precursor of methyl tertiary pentyl ether which is an octane value improving agent. t-Butyl alcohol obtained by using t-butyl hydroperoxide is a substance which is useful as a precursor of methyl-t-butyl ether which is an octane value improving agent.

The organic hydroperoxide used as a raw material may be diluted or dense purified material or non-purified material.

The olefin used in the present invention is not particularly restricted, and may be a non-cyclic, mono-cyclic, bicyclic or polycyclic compound and may be in the form of a monoolefin, diolefin or polyolefin.

When two or more olefin-type double bonds exist, they may be conjugated bond or non-conjugated bond. An olefin type compound having 2 to 60 carbon atoms is usually preferable. A compound having 3 to 40 carbon atoms is particularly preferable. Examples of such a monoolefin include ethylene, propylene, butene-1, isobutylene, hexene-1, hexene-2, hexene-3, octene-1, decene-1, styrene, and cyclohexene. Examples of the diolefin type hydrocarbon include butadiene and isoprene. These olefin type compound may have a substituent, and it is preferable that the substituent is a relatively stable group. Examples thereof include a halogen atom, and further, various substituents containing oxygen, sulfur or nitrogen atom together with hydrogen and/or carbon atom may exist. Examples of the substituted olefin type unsaturated compound include allyl alcohol, crotyl alcohol and allyl chloride.

An oxirane compound is a useful industrial chemical product. Propylene oxide can be converted to a useful polymer product also by polymerization reaction or copolymerization reaction. Epichlorohydrin obtained from allyl chloride is also an industrially important compound. Epichlorohydrin can be converted to glycerin. It is also possible to produce glycerin from an oxirane compound which is obtained from allyl alcohol.

The epoxidation reaction can be carried out in liquid-phase using a solvent and/or a diluting agent. The solvent and diluting agent should be a substance which is liquid under temperature and pressure in the reaction and is substantially inactive against reactants and products. The solvent may be composed of substance existing in a hydroperoxide solution used. For example, when ethylbenzene hydroperoxide (EBHP) is a mixture of EBHP with ethylbenzene which is a raw material thereof, it may also possible that a solvent is not particularly added and this is used as a solvent.

A second solvent can be used as a diluting agent, and as a solvent useful as the diluting agent, there are listed aromatic monocyclic compounds (for example, benzene, toluene, chlorobenzene, bromobenzene, orthodichlorobenzene), alkanes (for example, octane, decane, dodecane) and the like. An olefin type reactant in excess amount can also be used as a solvent. Namely, an olefin type reactant in excess amount can be used as a solvent together with the solvent added with the organic hydroperoxide. The total amount used of the solvents is preferably 20 mol or less (per 1 mol of hydroperoxide).

The epoxidation reaction temperature is usually from 0 to 200° C., and preferably from 25 to 200°C. The pressure may be a sufficient pressure to retain the reaction mixture in liquid form. In general, the pressure is advantageously from 100 to 10000 KPa.

After completion of the epoxidation reaction, a mixture in liquid form containing desired products can be separated from a catalyst composition. Then, the mixture in liquid form can be purified by a suitable method. The purification include fractional distillation, selective extraction, filtration, washing and the like. The solvent, catalyst, unreacted olefin, unreacted hydroperoxide can also be recycled and used again. The method of the present invention can be advantageously carried out using a catalyst in the form of a slurry, fixed bed. In the case of large scale industrial operation, it is preferable to use fixed bed. The method of the present invention can be carried out by a batch method, semi-continuous method or continuous method. When a solution containing reactants is passed through fixed bed, a mixture in liquid form exited from the reaction zone contains no catalyst or substantially no catalyst.

The present invention could provide a titanium-containing solid catalyst used for producing an oxirane compound by reacting an olefin type compound with an organic hydroperoxide, the catalyst having high activity and enabling the intended conversion in a smaller reactor than that of a conventional method The following examples illustrate the present invention (Influence of pore diameter of carrier)

EXAMPLE 1

Preparation of catalyst

Under nitrogen flow, to a solution of tetraisopropyl titanate (2.2 g) in isopropanol (20 ml) was added dropwise acetylacetone (1.6 g) slowly with stirring, then, the mixture was stirred for 30 minutes at room temperature. To a mixture of commercially available silica gel (10 to 20 mesh, surface area 326 m²/g, average pore diameter 10 nm)(50 g) with isopropanol (230 ml) was added dropwise the above-described solution, then the mixture was stirred for 1 hour at room temperature before the mixture was filtered. The solid portion was washed with isopropanol three times (total amount 250 ml). The solid portion was dried for 2 hours at 150° C. under air atmosphere. Further, it was dried for 4 hours at 600° C. under air atmosphere. This substance (10 g), hexamethyldisilazane (4 g) and toluene (50 g) were mixed, and the mixture was heated under reflux for 1 hour with stirring. Liquid was filtered off from the mixture. The residue was washed with toluene (100 g), and dried under reduced pressure (120° C., 10 mmHg, 3 hours) to obtain a catalyst. The amount of Ti (titanium) charge per unit surface area of the carrier was 0.5 $\mu$mol/m².

Synthesis of propylene oxide (PO) by reacting propylene with ethylbenzene hydroperoxide (EBHP)

Thus synthesized catalyst (3 g), 35% ethylbenzene hydroperoxide (24 g) and propylene (17 g) were charged in an autoclave equipped with a magnetic stirred, and reaction was effected at 90° C. for 1 hour. The reaction results are shown in Table 1.

EXAMPLE 2

A catalyst was obtained in the same manner as in Example 1 except that a carrier having an average pore diameter of 15 nm was used, amounts of teteraisopropyl titanate and acetylacetone were controlled so that the amount of Ti charge per unit surface area of the carrier was 0.5 $\mu$mol/m². The epoxidation reaction results are shown in Table 1.

EXAMPLE 3

A catalyst was obtained in the same manner as in Example 1 except that a carrier having an average pore diameter of 30 nm was used, amounts of teteraisopropyl titanate and acetylacetone were controlled so that the amount of Ti charge per unit surface area of the carrier was 0.5 $\mu$mol/m². The epoxidation reaction results are shown in Table 1.

EXAMPLE 4

A catalyst was obtained in the same manner as in Example 1 except that a carrier having an average pore diameter of 50 nm was used, amounts of teteraisopropyl titanate and acetylacetone were controlled so that the amount of Ti charge per unit surface area of the carrier was 0.5 $\mu$mol/m². The epoxidation reaction results are shown in Table 1.

COMPARATIVE EXAMPLE 1

A catalyst was obtained in the same manner as in Example 1 except that a carrier having an average pore diameter of 3 nm was used, amounts of teteraisopropyl titanate and acetylacetone were controlled so that the amount of Ti charge per unit surface area of the carrier was 0.5 $\mu$mol/m². The epoxidation reaction results are shown in Table 1.

In Table 1, activity is extremely low when a carrier having an average pore diameter of 3 nm is used. When it is 5 nm or more, activity is high. From these results, influence by the average pore diameter is apparent.

TABLE 1

(Ti concentration is 0.5 μmol/m².)

|  | Example | | | | Comparative example |
|---|---|---|---|---|---|
|  | 1 | 2 | 3 | 4 | 1 |
| Average pore diameter of carrier nm | 10 | 15 | 30 | 50 | 3 |
| Specific surface area m²/g | 326 | 198 | 116 | 79 | 560 |
| EBHP conversion %[*1] | 96.0 | 94.2 | 88.3 | 72.5 | 14.1 |
| PO selection ratio %[*2] | 84.8 | 90.1 | 91.6 | 91.9 | ([*3]) |

[*1]: EBHP conversion = consumed EBHP (mol)/charged EBHP (mol) × 100
[*2]: PO selection ratio = produced PO (mol)/consumed EBHP (mol) × 100
[*3]: reliable data was not obtained because of low activity (Water impregnation effect of carrier silica)

EXAMPLE 5

Preparation of catalyst

A commercially available silica gel (10 to 20 mesh, surface area 326 m²/g, average pore diameter 10 nm, 55 g) was impregnated in 2N HCl (200 g), and was allowed to stand still for 14 hours. It was filtered, and washed with deionized water until the filtrate became neutral. The solid was dried under reduced pressure (200° C., 2 mmHg, 2 hours) to obtain a pre-treated silica. Under nitrogen flow, to a solution of tetraisopropyl titanate (2.2 g) in isopropanol (20 ml) was added dropwise acetylacetone (1.6 g) slowly with stirring, then, the mixture was stirred for 30 minutes at room temperature.

To a mixture of the silica gel which had been subjected to water impregnation treatment as described above (50 g) with isopropanol (230 ml) was added dropwise the above-described solution, then the mixture was stirred for 1 hour at room temperature and then the mixture was filtered. The solid portion was washed with isopropanol (60° C., 20 hours). The solid portion was dried for 2 hours at 150° C. under air atmosphere. Further, it was calcined for 4 hours at 600° C. under air atmosphere. This substance (10 g), hexamethyldisilazane (4 g) and toluene (50 g) were mixed, and the mixture was heated under reflux for 1 hour with stirring. Liquid was filtered off from the mixture. The residue was washed with toluene (100 g), and dried under reduced pressure (120° C., 10 mmHg, 3 hours) to obtain a catalyst.

Synthesis of propylene oxide (PO) by reacting propylene with ethylbenzene hydroperoxide (EBHP)

Thus synthesized catalyst (Ti content based on charge 0.75% by weight, 3 g), 35% ethylbenzene hydroperoxide (24 g) and propylene (17 g) were charged in an autoclave equipped with a magnetic stirred, and reaction was effected at 90° C. for 1 hour. The reaction results are shown in Table 2.

EXAMPLE 6

A catalyst was obtained in the same manner as in Example 5 except that the solid portion was washed with isopropanol for three times at room temperature not at 60° C. The epoxidation reaction results are shown in Table 2.

EXAMPLE 7

A catalyst was obtained in the same manner as in Example 6 except that the water for the carrier water impregnation was HCl water having pH of 3. The epoxidation reaction results are shown in Table 2.

EXAMPLE 8

A catalyst was obtained in the same manner as in Example 7 except that the water for the carrier water impregnation was water having pH of 5.5. The epoxidation reaction results are shown in Table 2.

EXAMPLE 9

A catalyst was obtained in the same manner as in Example 8 except that the water for the carrier water impregnation was ammonia water having pH of 11. The epoxidation reaction results are shown in Table 2.

COMPARATIVE EXAMPLE 2

A catalyst was obtained in the same manner as in Example 5 except that a carrier which had not been subjected to water impregnation treatment was used. The epoxidation reaction results are shown in Table 3.

COMPARATIVE EXAMPLE 3

A catalyst was obtained in the same manner as in Example 6 except that a carrier which had not been subjected to water impregnation treatment was used. The epoxidation reaction results are shown in Table 3.

In Tables 2 and 3, it is shown that propylene oxide selection ratio does not change and about 2-fold increase in activity is obtained by conducting the carrier water impregnation (comparison of reaction speed constant). From these results, the effect of the carrier water impregnation is apparent.

TABLE 2

|  | Example | | | | |
|---|---|---|---|---|---|
|  | 5 | 6 | 7 | 8 | 9 |
| Carrier water impregnation condition | 2N HCl Water pH < 0.1 | 2N HCl Water pH < 0.1 | HCl Water pH = 3 | Water pH = 5.5 | NH₃ Water pH = 11 |
| Washing temperature | 60° C | Room temperature | Room temperature | Room temperature | Room temperature |
| EBHP conversion % | 99.6 | 99.8 | 99.7 | 99.7 | 99.5 |
| Reaction velocity constant k h⁻¹g-cat⁻¹ | 1.8 | 2.1 | 1.9 | 1.9 | 1.8 |
| PO selection ratio % | 90.8 | 84.9 | 86.3 | 85.2 | 87.7 |

TABLE 3

|  | Comparative example | |
|---|---|---|
|  | 2 | 3 |
| Carrier water impregnation condition | No impregnation | No impregnation |
| Washing temperature | 60° C. | Room temperature |
| EBHP conversion % | 95.5 | 96.0 |
| Reaction velocity constant k h⁻¹g-cat⁻¹ | 1.0 | 1.1 |
| PO selection ratio % | 90.0 | 84.8 |

• EBHP conversion = consumed EBHP (mol)/charged EBHP (mol) × 100
• k = 1n ((charged EBHP (mol)/remaining EBHP (mol)/catalyst weight (g)/reaction time (h))
• PO selection ratio = produced PO (mol)/consumed EBHP (mol) × 100

(Molar ratio of silanol group on carrier to metal Ti in titanium impregnation)

EXAMPLE 10

Preparation of catalyst

Under nitrogen flow, to a solution of tetraisopropyl titanate (0.37 g, $1.3 \times 10^{-3}$ mol) in isopropanol (10 ml) was added dropwise acetylacetone (0.27 g) slowly with stirring, then, the mixture was stirred for 30 minutes at room temperature. To a mixture of silica gel (25 g, silanol group number $2.2 \times 10^{-3}$ mol/g) with isopropanol (120 ml) was added dropwise the above-described solution, then the mixture was stirred for 1 hour at room temperature and then the mixture was filtered. The ratio (A/B) of the mol number (A) of metal titanium in the impregnation solution to the mol number (B) of a silanol group on the carrier was 0.02. Then, the solid portion was washed with isopropanol three times (total amount 120 ml). The solid portion was dried for 2 hours at 150° C. under air atmosphere. Further, it was calcined for 4 hours at 600° C. under air atmosphere. This substance (10 g), hexamethyldisilazane (4 g) and toluene (50 g) were mixed, and the mixture was heated under reflux for 1 hour with stirring. Liquid was filtered off from the mixture. The residue was washed with toluene (100 g), and dried under reduced pressure (120° C., 10 mmHg, 3 hours) to obtain a catalyst.

Synthesis of propylene oxide (PO) by reacting propylene with ethylbenzene hydroperoxide (EBHP)

Thus synthesized catalyst (3 g), 35% ethylbenzene hydroperoxide (24 g) and propylene (17 g) were charged in an autoclave equipped with a magnetic stirred, and reaction was effected at 90° C. for 1 hour. The reaction results are shown in Table 4.

EXAMPLES 11 TO 15 AND COMPARATIVE EXAMPLE 4

Catalysts were obtained in the same manner as in Example 10 except that the amounts of tetraisopropyl titanate and acetylacetone were controlled so that the mol number of metal titanate in the impregnation solution had a value shown in Table 4 or 5. The epoxidation reaction results are shown in Tables 4 and 5.

In Tables 4 and 5, when the ratio of the mol number of metal titanium in the impregnation solution to the mol number of a silanol group on the carrier is 0.2 or less, the selection ratio is higher as compared with the case in which the ratio is over 0.2. Apparently, it is important to limit the ratio to 0.2 or less for obtaining a catalyst having higher selection ratio.

TABLE 4

|  | Example | | | |
| --- | --- | --- | --- | --- |
|  | 10 | 11 | 12 | 13 |
| Silanol group on carrier[1] × $10^{-3}$ mol (B) | 55 | 50 | 58 | 61 |
| Metal titanium in impregnation solution[1] × $10^{-3}$ mol (A) | 1.3 | 1.3 | 2.6 | 3.9 |
| (A)/(B) | 0.02 | 0.03 | 0.04 | 0.06 |
| PO selection ratio[2] % | 92 | 92 | 90 | 85 |
| EBHP conversion[3] % *1 | 87 | 88 | 94 | 99.8 |

TABLE 5

|  | Example | | Comparative example |
| --- | --- | --- | --- |
|  | 14 | 15 | 4 |
| Silanol group on carrier[1] × $10^{-3}$ mol (B) | 45 | 45 | 45 |
| Metal titanium in impregnation solution[1] × $10^{-3}$ mol (A) | 3.9 | 7.8 | 11.5 |
| (A)/(B) | 0.09 | 0.17 | 0.26 |
| PO selection ratio[2] % | 85 | 82 | 79 |
| EBHP conversion[3] % *1 | 96 | 87 | 91 |

[1]amount per 25 g of carrier silica gel
[2]PO selection ratio = produced PO (mol)/consumed EBHP (mol) × 100
[3]EBHP conversion = consumed EBHP (mol) /charged EBHP (mol) × 100

What is claimed is:

1. A method for producing an oxirane compound in which an olefin type compound is reacted with an organic hydroperoxide in the presence of a titanium-containing solid catalyst, wherein the catalyst is obtained by at least one method selected from the following (1) to (3):
   (1) a titanium compound is supported on silica having an average pore diameter (D) measured by a mercury pressing method of 5 nm or more and having pore distribution in which at least 60% of pore volume is composed of pores having a pore diameter within the range of D±0.3 D (nm), and is calcined,
   (2) silica is impregnated in water, then dried, and a titanium compound is supported on the silica, then calcined,
   (3) silica is impregnated in a titanium-containing impregnation solution satisfying the following (formula 1), and is calcined:

$A/B \leq 0.2$ (formula 1)

A: mol number of metal titanium in the impregnation solution
   B: mol number of a silanol group existing in silica.

2. The method according to claim 1, wherein the olefin type compound is propylene.

3. The method according to claim 1, wherein the organic hydroperoxide is ethylbenzene hydroperoxide.

4. The method according to claim 1, wherein the olefin type compound is propylene and the organic hydroperoxide is ethylbenzene hydroperoxide.

5. The method according to claim 1, wherein the olefin type compound is propylene and the organic hydroperoxide is t-butyl hydroperoxide.

6. A method for producing an oxirane compound in which an olefin type compound is reacted with an organic hydroperoxide in the presence of a titanium-containing solid catalyst; wherein the titanium-containing solid catalyst is obtained by further silylation of a catalyst obtained by at least one method selected from the following (1) to (3):
   (1) a titanium compound is supported on silica having an average pore diameter (D) measured by a mercury pressing method of 5 nm or more and having pore distribution in which at least 60% of pore volume is composed of pores having a pore diameter within the range of D±0.3 D (nm), and is calcined,
   (2) silica is impregnated in water, then dried, and a titanium compound is supported on the silica, then calcined, (3) silica is impregnated in a titanium-containing impregnation solution satisfying the following (formula 1), and is calcined:

$$A/B \leq 0.2 \text{ (formula 1)}$$

A: mol number of metal titanium in the impregnation solution

B: mol number of a silanol group existing in silica.

7. The method according to claim 6, wherein the olefin type compound is propylene.

8. The method according to claim 6, wherein the organic hydroperoxide is ethylbenzene hydroperoxide.

9. The method according to claim 6, wherein the olefin type compound is propylene and the organic hydroperoxide is ethylbenzene hydroperoxide.

10. The method according to claim 6, wherein the olefin type compound is propylene and the organic hydroperoxide is t-butyl hydroperoxide.

* * * * *